(12) United States Patent
Okuno et al.

(10) Patent No.: US 7,874,729 B2
(45) Date of Patent: Jan. 25, 2011

(54) GENERAL IMAGING SYSTEM

(75) Inventors: Tomoharu Okuno, Kyoto (JP);
Masahiro Kawano, Kyoto (JP);
Mikihiko Kato, Kyoto (JP); Noboru Yamashita, Kyoto (JP); Goro Hirata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 41 days.

(21) Appl. No.: 12/516,116

(22) PCT Filed: Oct. 11, 2007

(86) PCT No.: PCT/JP2007/069878
§ 371 (c)(1),
(2), (4) Date: May 22, 2009

(87) PCT Pub. No.: WO2008/062611
PCT Pub. Date: May 29, 2008

(65) Prior Publication Data
US 2009/0257561 A1    Oct. 15, 2009

(30) Foreign Application Priority Data
Nov. 24, 2006    (JP)    .............................. 2006-317419

(51) Int. Cl.
*A61B 6/08* (2006.01)
(52) U.S. Cl. .................................................. 378/205
(58) Field of Classification Search ......... 378/115–117, 378/193–197, 205
See application file for complete search history.

(56) References Cited

U.S. PATENT DOCUMENTS

| | | | |
|---|---|---|---|
| 5,751,788 A | 5/1998 | Khutoryansky et al. | 378/197 |
| 6,302,580 B1 | 10/2001 | Dwyer, Jr. et al. | 378/197 |
| 2003/0194056 A1 | 10/2003 | Spahn | 378/205 |

FOREIGN PATENT DOCUMENTS

| | | |
|---|---|---|
| EP | 0373596 A1 | 6/1990 |
| JP | U62-36705 | 3/1987 |
| JP | 3-236832 | 10/1991 |
| JP | 06-165773 | 6/1994 |
| JP | 07-275230 | 10/1995 |
| JP | 10-179563 | 7/1998 |
| JP | 2006-034727 | 2/2006 |
| JP | 2006-149542 | 6/2006 |

*Primary Examiner*—Courtney Thomas
(74) *Attorney, Agent, or Firm*—McDermott Will & Emery LLP

(57) ABSTRACT

To automate positioning operation of an X-ray tube so as to reduce the inspection time. Anatomical program selection means selects a surgery method/imaging object portion so that an imaging condition stored as an anatomical program in advance is called out and set in an X-ray generation device. Here, when an operation switch is pressed, control means moves drive means built in X-ray irradiation means parallel movement holding means and X-ray irradiation means rotation holding means so as to obtain the positional relationship between an X-ray tube and an FPD stored in correspondence with the anatomical program (such as SID and incident angle). The position of the FPD should be matched with the examinee. However, since the positional relationship between the X-ray tube and the FPD is almost constant in accordance with the surgery method/imaging object portion, it is possible to reduce the time required for positioning the X-ray tube by using this configuration.

4 Claims, 4 Drawing Sheets

(a)　　　　　　　　　　　　(b)

(a)  (b)

(a)  (b)

GENERAL IMAGING SYSTEM

CROSS REFERENCE TO RELATED APPLICATIONS

This is a U.S. national phase application under U.S.C. §371 of International Patent Application No. PCT/JP2007/069878, filed Oct. 11, 2007 and claims the benefit of Japanese Application No. 2006-317419, filed Nov. 24, 2006. The International Application was published on May 29, 2008 as International Publication No. WO/2008/062611 under PCT Article 21(2). The contents of the above applications are incorporated herein in their entirety.

Field of Technology

The present invention relates to a clinical x-ray imaging device for creating an x-ray image of a body being examined, and in particular, relates to technology for positioning automatically the x-ray emitting means.

Background of the Invention

Conventionally, as this type of device there is, for example, a structure wherein x-ray emitting means are suspended so as to be able to move along the ceiling, and where the orientation of the x-ray emitting means can be adjusted. (See, for example, Japanese Unexamined Patent Application Publication H6-165773). In this device, the x-ray technician moves the x-ray emitting means manually as appropriate, to direct the x-ray and perform the imaging of the desired location.

When illuminating the body being examined using this device, the operator first positions the x-ray detecting means at the position of the body being examined that is to be imaged, and then positions the x-ray emitting means. The operator then exits the examination room, sets up the imaging conditions, and presses an imaging switch. Here the imaging conditions refer to conditions relating to the x-ray illumination, including at least the tube voltage of the x-ray emitting means for the x-ray that will be directed at the body being examined, the tube current, and the emission time. The imaging conditions include conditions such as the optical field using a phototimer, and the like.

In this series of operations, the operation for positioning the x-ray emitting means is the most time-consuming given that there are a plurality of axes of movement, and that it is necessary to position the x-ray emitting means facing the x-ray detecting means that are hidden by the body being examined.

In contrast to the device set forth above, a device has been produced for moving the x-ray emitting means automatically in the vertical direction so that the x-ray emitting means will face the x-ray detecting means. A device that is structured so as to move the x-ray emitting means and the x-ray detecting means automatically has been proposed as a further advancement. For example, when the same body to be examined was imaged previously, the positions of the x-ray emitting means and the x-ray detecting means were stored together with the captured image, in a structure which then moves the x-ray emitting means and the x-ray detecting means to those locations. (See, for example, Japanese Unexamined Patent Application Publication 2006-149542).

On the other hand, it is necessary for the operator to set up the imaging conditions for each image. However, setting these up individually is quite time-consuming because it is not possible to set the imaging conditions without having a substantial amount of knowledge regarding radiation imaging. Here typical imaging conditions are established in general if the procedure, position of the body to be imaged, direction of imaging, and similar conditions are established.

Given this, there has been a proposal for a system capable of enabling imaging conditions to be recalled intuitively using abbreviated procedures through storing anatomical programs in the equipment in advance for selection by the operator. (See, for example, Japanese Unexamined Patent Application Publication H7-275230). Here the anatomical programs refer to data structures that are associated with imaging conditions and, at least, imaging methods including the procedure and the image target position on the body to be imaged.

In the general imaging system according to the prior art it is not possible to position the x-ray emitting means automatically when examining a new body to be examined. There are few cases where there are repetitive examinations of the body to be examined, where, in most cases, there is a problem in that the positioning must be done manually.

Additionally, even if there is equipment that automatically positions the height of the x-ray emitting means so as to face the x-ray detecting means, there is a problem in that the automatic positioning must be done after first determining the angle of the x-ray emitting means. In particular, in a system that includes a plurality of x-ray detecting means, such as a system that can be used while erect or supine, the angle of the x-ray emitting means is determined so as to have an appropriate incident angle relative to the x-ray detecting means subject to imaging, and thus there are many opportunities for adjusting the angle of the x-ray emitting means. Fundamentally, even if there is an automatic positioning function, the elongated time is extended because of the need to perform operations for adjusting the angle of the x-ray emitting means each time.

The object of the present invention is to provide a mechanism for effective automatic positioning of the x-ray emitting means, thereby reducing the time required for the examination.

SUMMARY OF THE INVENTION

The inventors have solved the problems set forth above through a structure that has the distinctive features described below, focusing on determining the distance between, at least, the x-ray detecting means and the x-ray emitting means (typically called the SID (source-image-distance) or the FFT (film-focal-distance), and on the angle of the x-ray emitting means, or in other words, the x-ray incident angle onto the x-ray detecting means, depending on conditions that are set in the anatomical program, regardless of the body to be examined, when automating the positioning of the x-ray emitting means.

In other words, the general imaging system includes an x-ray emitting means; an x-ray detecting means; an x-ray detecting means moving/holding means for holding the x-ray detecting means movably; an x-ray emitting means rotating/holding means for holding the x-ray emitting means rotatably; an x-ray emitting means moving/holding means for holding the rotating/holding means rotatably; a rotational driving means for driving the x-ray emitting means so as to rotate relative to the rotating/holding means; a driving means for driving the moving/holding means so as to move; position detecting means for detecting the rotational angle of the x-ray emitting means, the position of the x-ray detecting means, and the positional relationship with the x-ray emitting means.

The system also includes a storing means for storing anatomical programs and the rotational angle of the x-ray emitting means, and the positional relationship of the x-ray emitting means from the position of the x-ray detecting means, in accordance with the anatomical programs; anatomical program selecting means for selecting an anatomical program that has been stored in the storing means; controlling means for controlling the rotational driving means and the driving means based on the rotational angle of the x-ray emitting means and the positional relationship of the x-ray emitting means from the position of the x-ray detecting means, and the stored detection results of the position detecting means, in relation to the selected anatomical program; and an operating switch for detecting an operation by the operator to issue a control instruction to the controlling means.

Additionally, the general imaging system set forth above, further has a recording means for recording, to the storing means, the rotational angle of the x-ray emitting means, the position of the x-ray detecting means, and the positional relationship with the x-ray emitting means.

The invention as set forth above, wherein the recording means record the rotational angle of the x-ray emitting means and the positional relationship of the x-ray emitting means from the position of the x-ray detecting means, detected by the position detecting means.

The invention further include anatomical program automatic transitioning means for selecting the subsequent anatomical program automatically after imaging.

Given the invention the operator first positions the x-ray detecting means at the target location of the body to be examined. Next, through the selection of an anatomical program on the operating panel, the rotational angle of the x-ray emitting means, and the positional relationship between the x-ray detecting means and the x-ray emitting means are read out in accordance with to selected anatomical program. Thereafter, the operating switch is pressed to move the x-ray emitting means so as to be at the rotational angle of the x-ray emitting means, and with the positional relationship between the x-ray detecting means and the x-ray emitting means, that have been read out. After the movement of the x-ray emitting means has been completed, the operator presses an imaging switch to perform the imaging.

This has the effect of enabling the examination period to be compressed, without requiring manipulation of the x-ray emitting means.

Furthermore, given the invention as set forth above, the relationship between the anatomical program, the rotational angle of the x-ray emitting means and positional relationship of the x-ray emitting means with the x-ray detecting means are changed by the recording means.

The relationship between the anatomical program, the rotational angle of the x-ray emitting means and positional relationship of the x-ray emitting means with the x-ray detecting means can be changed based on the experience, etc., of the operator.

Note that if there is no change by the recording means, then the existing rotational angle of the x-ray emitting means and positional relationship of the x-ray emitting means with the x-ray detecting means will be used. The pre-existing information may be stored in the storing means in advance, such as at the time of shipping from the factory.

Given the invention as set forth above, the recording means can record to the storing means the rotational angle of the x-ray emitting means and the positional relationship of the x-ray emitting means with the position of the x-ray detecting means, detected by the position detecting means. That is, the current status of the x-ray emitting means can be recorded.

The operator is able to view, and record intuitively, the current positional relationship of the equipment. This enables a method of use wherein, for example, the x-ray emitting means are positioned manually first in the anatomical program for imaging, and that position is recorded if the imaging turns out well.

Given the invention as set forth above, the subsequent anatomical program can be selected automatically through the anatomical program automatic transitioning means after imaging is performed. Consequently, pushing the operating switch once imaging has been completed causes the x-ray emitting means to move to the positions corresponding to the subsequent anatomical program.

In the case wherein imaging is performed on the same body continuously from different directions, it is possible to perform the imaging continuously without entering the examination room. This functions effectively when, for example, imaging the lung field of the body to be examined from the front and from both sides.

DETAILED DESCRIPTION OF THE INVENTION

Figures 1, 2:
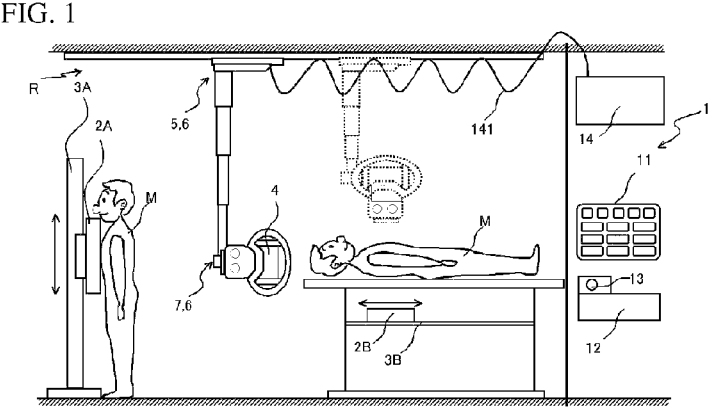
FIG. 1 is a diagram for explaining the overall structure of the present invention.
FIG. 2 is a diagram for explaining in detail the erect stand.

A summary of a general imaging system according to the present invention is illustrated in FIG. 1. Here the explanation uses, as an example, a system typically known as an erect/supine system.

When imaging the body to be examined M in the erect state, the imaging is performed by causing the x-ray tube 4, as the x-ray emitting means, to face an FPD (flat panel detector) 2A, as the x-ray detecting means, that is supported movably in the vertical direction relative to the erect stand 3A, as the x-ray detecting means holding means. The FPD 2A has the function of converting the x-rays into an image, where the image is displayed on a monitor, not shown.

Similarly, when imaging the body to be examined M in the supine state, imaging is performed by causing the x-ray tube 4, as the x-ray emitting means, to face an FPD 2B that is held movably in the lengthwise direction of the body to be examined, relative to the supine table 3B, as the x-ray detecting means holding means.

In either case, the method/imaging target position, etc., are selected by the anatomical program selecting means 11 to read out the imaging conditions that are stored in advance as an anatomical program, to thereby set up those conditions in the x-ray generating device 14. The x-ray generating device 14 controls the x-ray tube 4, through a cable 141, to emit x-rays of the appropriate imaging conditions.

At this time, the operating switch 13 is pressed to cause the controlling means 12 to operate the driving means 6, which are housed within the x-ray emitting means parallel movement/holding means 5 and the x-ray emitting means rotating/holding means 7 so as to achieve the positional relationship (for example, the SID and the incident angle) between the x-ray tube 4 and the FPD 2 that is stored in relation to the anatomical program.

The details for each portion will be explained below.

The details of the x-ray detecting means holding means will be explained first. FIG. 2(a) is a side view diagram of the erect stand 3A, as the x-ray detecting means holding means, and FIG. 2(b) is a cross-sectional diagram along A-A' in FIG. 2(a).

The erect stand 3A is structured from a pulley 35 that is secured on the inside of a support pillar 31, a wire 34 that is attached to the pulley 35, a counterweight 33 that is attached to one end of the wire 34, a holding portion 36 that is attached to the other end, and an electromagnetic lock 32 for holding the holding portion 36 stationary relative to the support pillar 31. The holding portion 36 is secured to the FPD 2A.

Additionally, a potentiometer 91A is connected as the position detecting means, to the rotational axis of the pulley 35, where the axis of the potentiometer 91A is structured so as to rotate together with the rotation of the pulley 35. This structure converts the position of the FPD 2A, which is secured to the holding portion 36, into a resistance value for the potentiometer 91A. Here the support pillar 31 is rigidly secured to the examination room R. Consequently, the position of the FPD 2A in the examination room R can be calculated from the resistance value of the potentiometer 91A.

Furthermore, a lock releasing switch 37 is provided on the side surface of the holding portion 36. While the lock releasing switch 37 is depressed, the electromagnetic lock 32 is released, enabling the holding portion 36 to move upward or downward.

The supine table 3B is structured similarly to the erect stand 3A, except for the movement of the FPD 2A being in the horizontal direction and except for the tabletop between the FPD 2B and the body to be examined M.

The x-ray emitting means parallel movement mechanism 5 will be explained in detail next.

Figure 3:
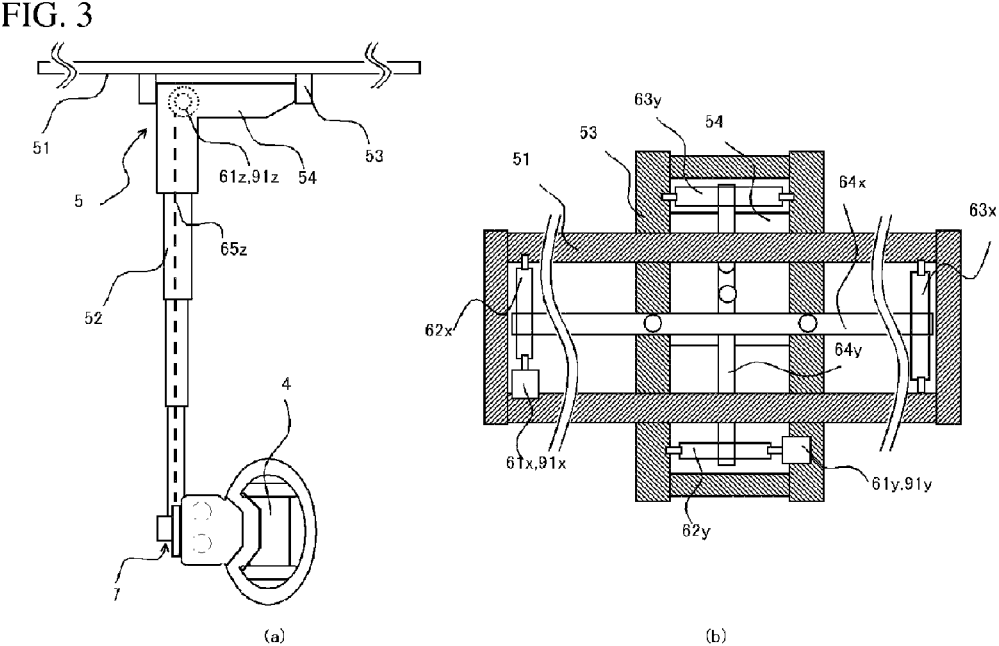
FIG. 3 is a diagram for explaining in detail the x-ray emitting means parallel movement mechanism.

FIG. 3(a) is a front view diagram of the x-ray emitting means parallel movement mechanism 5. FIG. 3(b) is a diagram when FIG. 3(a) is seen from above.

The x-ray emitting means parallel movement mechanism 5 is structured from a ceiling rail 51, a movable rail 53 that is connected so as to enable parallel movement along the ceiling rail 51, a stationary portion 54 that is connected so as to enable parallel movement along the movable rail 53, and an extendable arm 52 that is connected to one end of the stationary portion 54. Note that the x-ray emitting means rotating/holding means 7 are connected to the other end of the extendable arm 52, and the x-ray tube 4 is held by the x-ray emitting means rotating/holding means 7.

The structure for moving the x-ray tube forth in the parallel direction (defined as the x direction) will be explained. A motor-side roller $62x$, a motor $61x$ for rotating the motor-side roller $62x$, and a potentiometer $91x$ that is attached to the rotational axis of the motor $61x$ are disposed on one end of the ceiling rail 61. An opposite-side roller $63x$ is disposed on the other end of the ceiling rail 51. A timing belt $64x$ is connected between the motor-side roller $62x$ and the opposite-side roller $63x$. The movable rail 53 is secured to the timing belt $64x$. Given this structure, the x-ray tube 4 can be moved in the x direction. Furthermore, the position of the x-ray tube 4 in the x direction can be calculated from the resistance value of the potentiometer $91x$.

The structure for moving the x-ray tube 4 in the direction parallel to the movable rail 53 (defined as the y direction) will be explained. a motor-side roller $62y$, a motor $61y$ for rotating the motor-side roller $62y$, and a potentiometer $91y$ that is attached to the rotational axis of the motor $61y$ are disposed on one end of the movable rail. An opposite-side roller $63y$ is disposed on the other end of the movable rail 53. A timing belt $64y$ is connected between the motor-side roller $62y$ in the opposite-side roller $63y$. The movable rail 53 is secured to the timing belt $64y$. This structure enables the x-ray tube 4 to be moved in the y direction. Additionally, the position of the x-ray tube 4 in the y direction can be calculated from the resistance value of the potentiometer $91y$.

The mechanism for moving the x-ray tube 4 in the vertical direction (defined as the z direction) will be explained. A windup motor $61z$, a potentiometer $91z$ that is attached to the rotational axis of the motor $61z$, and a wire $65z$, connected on one end to the motor $61z$ and connected on the other end to the extendable arm 52 are housed in the stationary portion 54. The motor $61z$ is rotated to wind up the wire $65z$, to cause the extendable arm 52 to extend or retract. This mechanism enables the x-ray tube 4 to be moved in the z direction. Additionally, the position of the x-ray tube 4 in the z direction can be calculated from the resistance value of the potentiometer $91z$. Note that normally the extension and retraction of the extendable arm 52 is balanced by a spring balancing mechanism.

These structures enable the x-ray tube 4 to be moved in the x, y, and z directions. Additionally, because the ceiling rail 51 is secured to the ceiling of the examination room R, the position of the x-ray tube 4 in the examination room R can be calculated from the individual resistance values of the potentiometers $91x$, $91y$, and $91z$. Note that in the x-ray emitting means rotating/holding means 7, explained next, it is necessary to calculate the position of the x-ray tube 4 taking the rotational angle thereof into consideration as well when the rotational axis thereof is offsetted.

Figure 4:
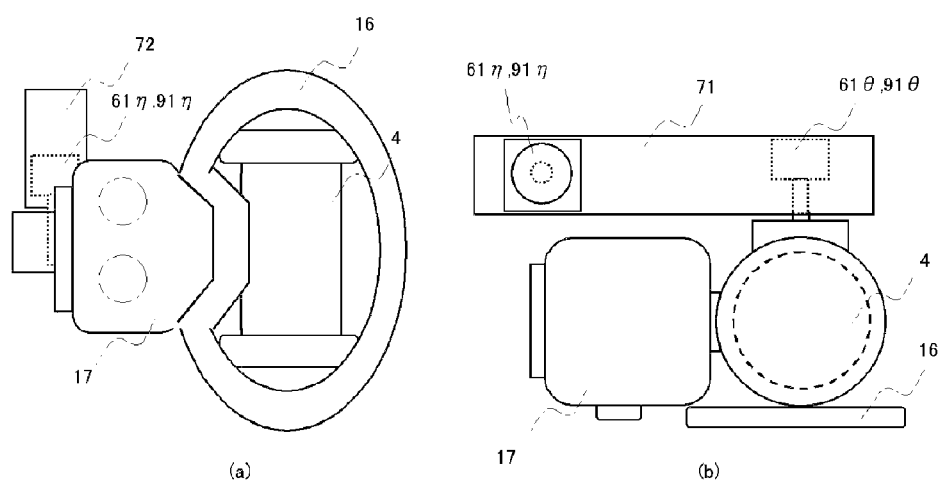
FIG. 4 is a diagram for explaining in detail the x-ray emitting means rotating mechanism.

The x-ray emitting means rotating/holding means 7 will be explained in detail. FIG. 4(a) is a front view of the x-ray emitting means rotating/holding means 7. FIG. 4(b) is a diagram when FIG. 4(a) is viewed from above.

The rotating/holding means 71 for rotating around the horizontal axis, which rotates the x-ray tube 4 around the horizontal axis (hereinafter termed the $\theta$ direction) will be explained first. A motor $61\theta$, and a potentiometer $91\theta$ that is connected to the rotational axis of the motor $61\theta$, are housed in the rotating/holding means 71 for rotating around the horizontal axis. The motor $61\theta$ is also connected to the x-ray tube 4. This structure enables the x-ray tube 4 to be moved in the $\theta$ direction. Furthermore, the rotational angle of the x-ray tube 4 in the $\theta$ direction can be calculated from the resistance value of the potentiometer $91\theta$.

The rotating/holding means 72 for rotating around the vertical axis, which rotates the x-ray tube for around the vertical axis (hereinafter termed the $\eta$ direction) will be explained next. A motor $61\eta$, and a potentiometer $91\eta$ that is connected to the rotational axis of the motor $61\eta$ are housed within the rotating/holding means 72 for rotating around the vertical axis. The motor $61\eta$ is also connected to the rotating/holding means 71 for rotating around the horizontal axis. This structure enables the x-ray tube 4 to be rotated in the $\eta$ direction. Also, the rotational angle of the x-ray tube 4 in the $\eta$ direction can be calculated from the resistance value of the potentiometer $91\theta$.

Note that a collimator 17 and a handle 16 are attached to the x-ray tube 4, the same as in the conventional general imaging device. Furthermore, although the explanation thereof is omitted due to lack of direct relevance to the present invention, electromagnetic locks are provided for locking movement and rotation in each of the x, y, z, $\theta$, and $\eta$ directions for each of these portions of the x-ray emitting means parallel movement/holding means 5 and x-ray emitting means rotating/holding means 7, where a lock release switch that is equipped on the handle 16 can be depressed to release the locks individually, to enable the x-ray tube 4 to be moved or rotated manually. Even when being driven by the motor, the motor can be rotated after releasing these electromagnetic locks individually.

Figure 5:
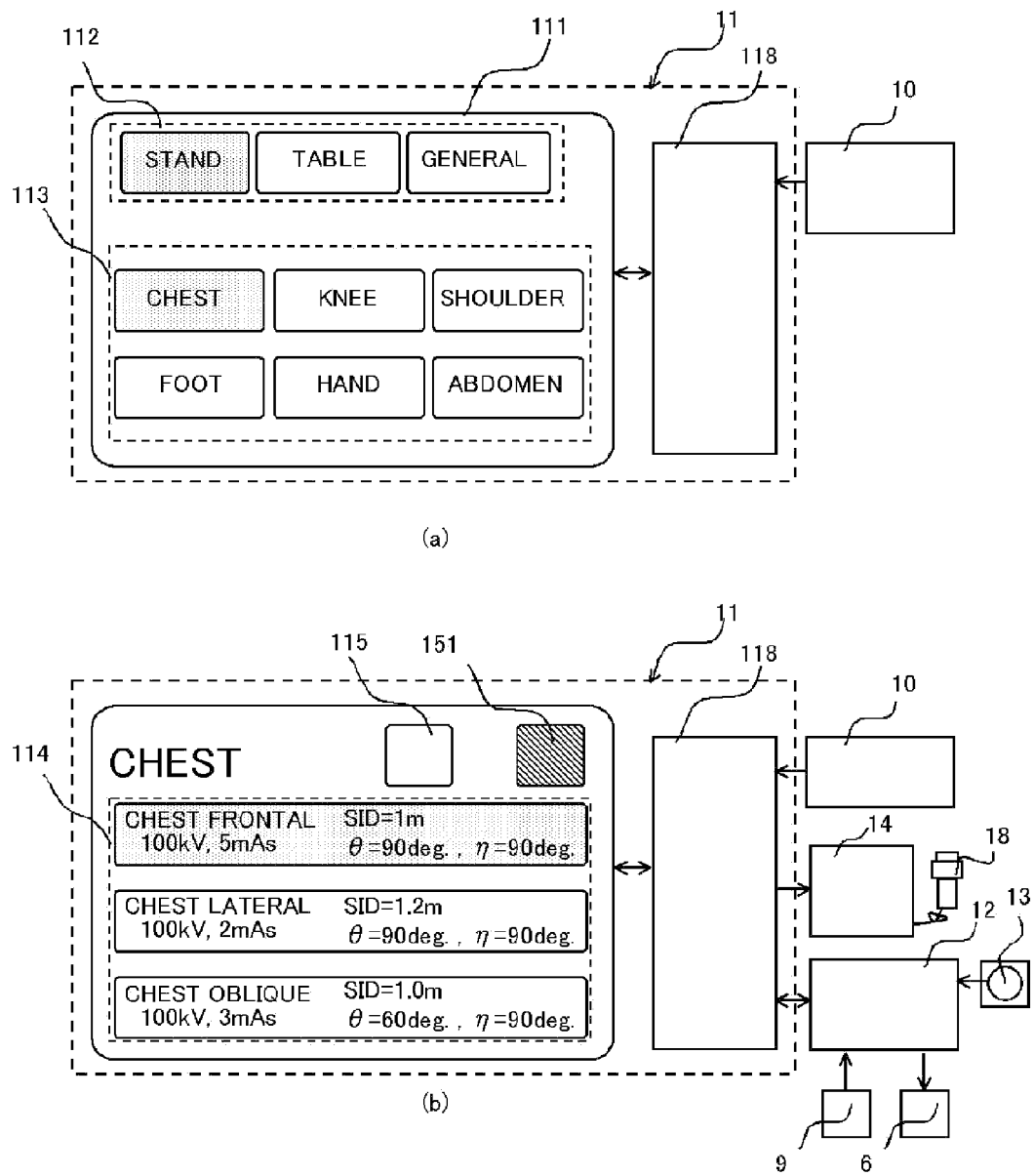
FIG. 5 is a diagram for explaining the anatomical program selecting means and the associated mechanisms.

The details of the anatomical program selecting means 11 will be explained next. FIG. 5(*a*) is a diagram for explaining the method and imaging target position selecting screen. FIG. 5(*b*) is a figure for explaining the screen that is displayed when the imaging target position has been selected in FIG. 5(*a*).

The anatomical program selecting means 11 are structured from a liquid crystal touch panel 111 and input/display controlling means 118 for detecting a touch panel input in the liquid crystal touch panel 111 and for controlling of the liquid crystal display.

The input/display controlling means 118 read out the details of the anatomical programs that are stored in the storing means 10, and display them onto the liquid crystal touch panel 111. The anatomical programs are categorized by method, and are further divided into categories by the imaging target position within each method. For each imaging target position, the steps that are necessary when imaging the position are stored. For a single step, the imaging conditions and the positional relationship between the x-ray tube 4 and the FPD 2 are stored. The optimal imaging conditions and positional relationship between devices for the examination can be set automatically through making a selection by tracing down the hierarchical classifications.

The behavior when the imaging the chest region in the erect position using this configuration will be explained.

The operator causes the body to be examined M to stand in front of the erect stand 3A, aligns the FPD 2A to the chest region, and exits the examination room R. (See FIG. 1.)

Next, with the screen display status as in FIG. 5(*a*), the operator pushes the "STAND" switch of the method selecting switches 112. The input/display controlling means 118 detect this operation, and read out, from the memory 10, the list of imaging target positions belonging to the method "STAND," and display them on the imaging target position selecting switches 113.

The operator then pushes the "CHEST" switch of the imaging target position selecting switches 113. The input/display controlling means 118 detect this operation and read out, from the memory 10, a list of steps belonging to the imaging target position "CHEST" of the method "STAND," and displays them on the step selecting switches 114, as illustrated in FIG. 5(*b*). On the switch for each step, the imaging direction (FRONTAL, LATERAL, OBLIQUE), the imaging conditions (tube voltage and tube current-time product), and the positional relationship between the x-ray tube 4 and the FPD 2 (the SID and the incident angle) are displayed. In the initial state, the first step is selected (that is, the applicable switch is highlighted).

The controlling means 12 obtains, from the position detecting means 1, the current position $P_A$ of the FPD 2A in the coordinate system of the examination room, the current position $P_S$ (x, y, z) of the x-ray tube 4, and the current rotational angle $Q_S$ (θ, η). Here the coordinate system in the coordinate system of the examination room will be explained in reference to FIG. 6.

Figure 6:
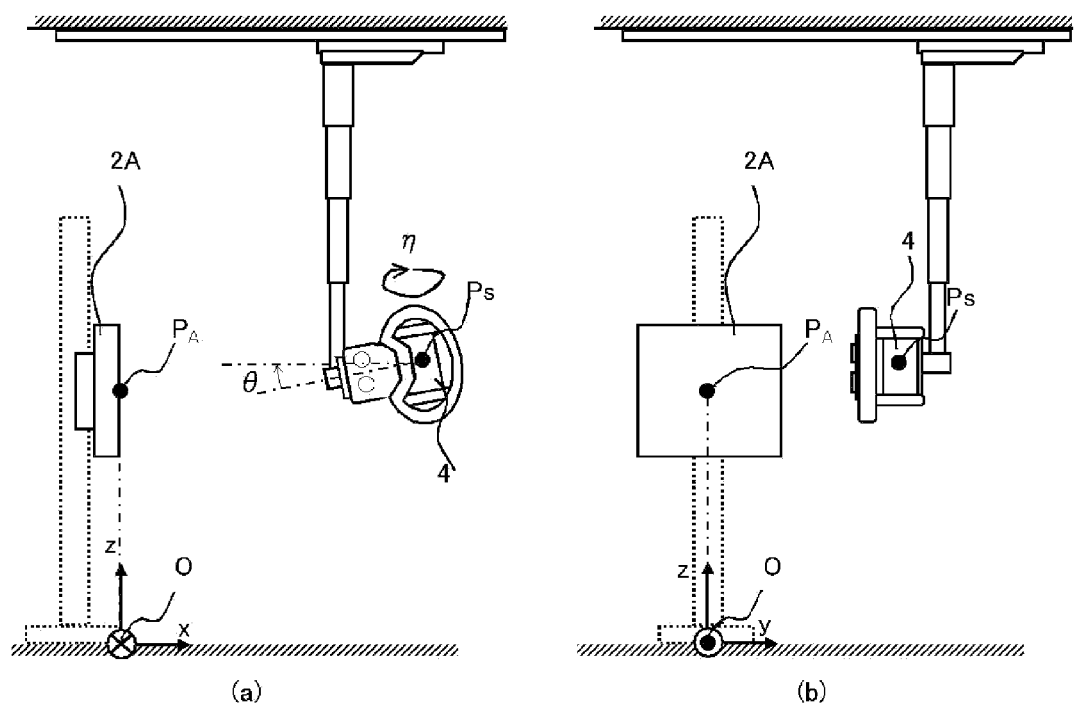
FIG. 6 is a diagram for explaining the examination room coordinate system.

Here FIG. 6(*a*) is a diagram of the general imaging system, including the erect stand 3A, when viewed from the side surface of the FPD 2A, where the direction to the right on the surface of the paper is defined as x, the direction of depth is defined as y, and the upward direction is defined as z. Similarly, FIG. 6(*b*) is a diagram when viewed from the front surface of the FPD 2A, where the direction to the right on the surface of the paper is y, the forward direction (that is, out of the paper) is x, and the upward direction is z.

The position detecting means 9 apply a reference voltage across the stationary electrodes of the potentiometer 91A, and perform an A/D conversion of the voltage value at the movable electrode, to obtain the voltage value VA. The position detecting means 9 has measured the voltages at two locations, with the FPD 2A having been moved, in advance, and stored those voltages together with the positions. For example, let us assume that the voltage value $V_{A1}$ at the position $P_{A1}$=1 m and the voltage value $V_{A2}$ at the position $P_{A2}$=2 m have been stored. The position detecting means 9, being structured in this way, substitute the current voltage value VA into a linear interpolation formula using the voltage values $V_{A1}$ and $V_{A2}$ at the position is $P_{A1}$ and $P_{A2}$, to calculate the current height ZA of the FPD 2A. The FPD 2A is positioned at the origin O of the examination room coordinate system, and so the position $P_A$ (X, y, z) of the FPD 2A=(0, 0, ZA).

Similarly, the position detecting means 9 apply reference voltage across the stationary terminals of the potentiometers 91x, 91y, 91z, 91θ, and 91η relating to the x-ray tube 4, and perform A/D conversion on the voltage values for the movable terminals to obtain the voltage values Vx, Vy, Vz, Vθ, and Vη, to calculate the current position $P_S$ (x, y, z) and the relative rotational angle $Q_S$ (θ, η) through linear interpolation.

The controlling means 12 obtain the aforementioned $P_A$, $P_S$, and $Q_S$ from the position detecting means 9. Additionally, the SID (=1 m) and the incident angle (=90°) corresponding to the step that is currently selected are obtained from the input/display controlling means 118, and are applied to the $P_A$ to calculate the relative target position $P_{SO}$ (x, y, z) and target rotational angle $Q_{SO}$ (θ, η) of the x-ray tube 4.

If the $P_S$ and $Q_S$ obtained do not match the $P_{SO}$ and $Q_{SO}$, the controlling means 12 flash an LED that is housed within the operating switch 13. The LED is turned OFF if these values match.

When the operating switch 13 is flashing, the operator presses the operating switch 13. When the operating switch 13 is pressed, the controlling means 12 controls the individual motors 61x, 61y, 61z, 61θ, and 61η, which are connected to the driving means 6, while calculating the current relative positions $P_S$ and $Q_S$ of the x-ray tube 4, using the position detecting means 91 iteratively, so that these relative positions $P_S$ and $Q_S$ will match $P_{SO}$ and $Q_{SO}$. While the driving means 6 are driving, the LED housed with in the operating switch 13 will be illuminated. The LED is turned OFF when the target position and target rotational angle are achieved.

The operator confirms that the LED of the operating switch 13 has been turned OFF, and then presses the imaging switch 18. The x-ray generating device 14 obtains the imaging conditions corresponding to the step currently selected by the input/display controlling means 118, and an x-ray is emitted from the x-ray tube 4 based on the imaging conditions thus obtained. When the x-ray has been emitted, the x-ray generating device 14 provides notification, to the input/display controlling means 118, that the imaging has been completed.

The input/display controlling means 118, having received the notification of completion of the imaging, automatically puts the subsequent step ("LATERAL") into the selected state. The operator instructs the body to be imaged M to turn to the side. Thereafter, the operator presses the operating switch 13 to move to the x-ray tube 4, and then presses the imaging switch 18 to perform the imaging.

The RETURN switch 115 is pressed when another position is to be imaged or when the method is to be changed. When the RETURN switch 115 is pressed, the input/display controlling means 118 returns to the display state of FIG. 5(a).

If, at this point, the operator wishes to change the positional relationship between the x-ray tube 4 and the FPD 2 that has been stored in advance, then the operator moves the x-ray tube 4 to the appropriate position using manual operations, and presses the RECORD switch 151, which is the recording means. When the RECORD switch 151 has been pressed, then the input/display controlling means 118 obtain the current SID and rotational angle from the controlling means 12, and overwrite the storing means 10.

While, in the above, the structure and operation of a general imaging system according to the present invention have been explained, these are no more than an example of embodiment, and the structure is not limited thereto.

The FPD is an illustrative example of an x-ray detecting means, and various different embodiments thereof may be selected, insofar as a variable density image of the x-ray can be obtained, such as the use of a cassette, a CR, and I. I., or the like.

While the erect stand and the supine table were given as illustrative examples of the x-ray detecting means holding means, a variety of embodiments may be selected insofar as the x-ray detecting means are held so as to be movable in at least one direction. For example, tiltable table erect stands and supine tables capable of parallel movement in multiple directions are also included in x-ray detecting means holding means.

While an x-ray tube was given as an illustrative example of x-ray emitting means, the embodiment may be changed in a variety of ways insofar as there is the capability of emitting x-rays.

Additionally, while a combination of a ceiling rail, a movable rail, and an extendable arm was presented as an illustrative example of x-ray emitting means parallel movement holding means, the embodiment may be varied in a variety of ways, insofar as the structure is capable of parallel movement in at least one direction relative to the examination room. For example, the arm may be secured to the floor instead of the ceiling.

Additionally, while a motor was presented as an illustrative example of driving means, the embodiment may be varied in a variety of ways insofar as there is the function of being able to change the position of an object. There is, of course, no limitation to a method of driving using a timing belt or a wire.

Additionally, while a potentiometer was presented as an illustrative example of the position detecting means, the means may be varied in a variety of ways insofar as they are capable of converting the position into an electrical magnitude. For example, a rotary encoder or an ultrasonic sensor, or the like, may be used instead. Additionally, instead of being able to measure the positions of the x-ray detecting means and the x-ray emitting means individually, the position detecting means also includes means capable of measuring the distance and incident angle between the x-ray detecting means and the x-ray emitting means directly.

Note that imaging conditions associated with simple serial numbers or elements that identify individual bodies to be measured, such as names, are not included in the anatomical programs in the present invention.

The present invention can be used in the medical industry, which performs that examinations using x-rays.

The invention claimed is:

1. A general imaging system comprising:
an x-ray emitter;
an x-ray detector;
an x-ray detector moving/holding device holding the x-ray detector movably;
an x-ray emitter rotating/holding device holding the x-ray emitter rotatably;
an x-ray emitter moving/holding device holding the rotating/holding device rotatably;
a rotational driver driving the x-ray emitter to rotate relative to the rotating/holding device;
a driver driving the moving/holding devices to move;
a position detecting device for detecting the rotational angle of the x-ray emitter, the position of the x-ray detector, and the positional relationship with the x-ray emitter;
a storage for storing anatomical programs and the rotational angle of the x-ray emitter, and the positional relationship of the x-ray emitter from the position of the x-ray detector, in accordance with the anatomical programs;
an anatomical program selecting device selecting an anatomical program stored in the storage;
a controller controlling the rotational driver and the driver based on the rotational angle of the x-ray emitter and the positional relationship of the x-ray emitter from the position of the x-ray detector, and the stored detection results of the position detecting device, in relation to the selected anatomical program; and
an operating switch detecting an operation by the operator to issue a control instruction to the controlling means.

2. A general imaging system set forth in claim 1, further comprising:
recording device recording, to the storage, the rotational angle of the x-ray emitter, the position of the x-ray detector, and the positional relationship with the x-ray emitter.

3. A general imaging system set forth in claim 2, wherein: the recording device records the rotational angle of the x-ray emitter and the positional relationship of the x-ray emitter from the position of the x-ray detector detected by the position detecting means.

4. A general imaging system as set forth in claim 1, further comprising an anatomical program automatic transitioning device selecting the subsequent anatomical program automatically after imaging.

* * * * *